United States Patent
Schmitt et al.

(10) Patent No.: US 7,157,238 B2
(45) Date of Patent: Jan. 2, 2007

(54) DIAGNOSTIC AND THERAPEUTIC USE OF ANTIBODIES AGAINST THE UROKINASE RECEPTOR

(75) Inventors: Manfred Schmitt, München (DE); Frank Noack, Lübeck (DE); Henner Graeff, München (DE); Nadja Harbeck, München (DE)

(73) Assignee: Wilex AG, Munich (DE)

( * ) Notice: Subject to any disclaimer, the term of this patent is extended or adjusted under 35 U.S.C. 154(b) by 0 days.

(21) Appl. No.: 09/926,323

(22) PCT Filed: Dec. 13, 2000

(86) PCT No.: PCT/EP00/03347

§ 371 (c)(1),
(2), (4) Date: Mar. 5, 2002

(87) PCT Pub. No.: WO00/62071

PCT Pub. Date: Oct. 19, 2001

(65) Prior Publication Data

US 2004/0214245 A1 Oct. 28, 2004

(30) Foreign Application Priority Data

Apr. 13, 1999 (EP) .................................. 99107199

(51) Int. Cl.
G01N 33/574 (2006.01)

(52) U.S. Cl. ............. 435/7.92; 530/387.3; 530/388.85; 530/391.3

(58) Field of Classification Search .................. 435/7, 435/7.92; 530/387.3, 388.85, 391.3
See application file for complete search history.

(56) References Cited

U.S. PATENT DOCUMENTS 5,234,816 A * 8/1993 Terstappen
5,519,120 A * 5/1996 Dano et al.
6,638,502 B1 * 10/2003 Li et al.

FOREIGN PATENT DOCUMENTS

EP 0317156 A 5/1981

OTHER PUBLICATIONS

McHugh et al J immuno methods 1986 95:57-61, Abstract Only.*
Fundamental Immunology 242 (William E. Paul, M.D. ed., 3d ed. 1993).*
Rudikoff et al (Proc Natl Acad Sci USA vol. 79 p. 1979.*
Tockman et al, Cancer Research vol. 52 p. 2711s (1992).*
Janicke et al Fibrinolysis vol. 4 p. 69 (1990).*
W. Xue et al.: Urokinase-type plasminogen activator receptors associate with beta1 and beta 3 integrins of fibrosarcoma cells: dependence on extracellular matrix components: Cancer Research vol. 57, No. 9, May 1, 1997, pp. 1682-1689, XP002117246 Baltimore, MD, VSA abstract; figure 1.
T. Luther et al.: "Epitope-mapped monocolonal antibodies as tools for functional and morphological analyses of the human urokinase receptor in tumor tissue" American Journal of Pathology, vol. 150 No. 4, Apr. 1997, pp. 1231-1244, XP002117251 Hagerstown, MD, VSA cited in the whole document.
R. Todd et al.: "CD87 Workshop Panel report (p. 1016-1020 in 'Leucocyte Typing VI', Eds. T. Kishimoto et al.)" 1997, Garland Publishing, Inc. XP002117252 Cited in the application figures tables.
V. Magdolen et al.: "Epitope-mapped monoclonal antibodies directed to the human urokinase receptor (uPAR, CD87)," Tissue Antigens, vol. 48, No. 4-2, Oct. 1996, p. 424 XP000929590 Kopenhagen, Dänemark Abstract MC-2-02.
K. Fischer et al.: "Urokinase induces proliferation of human ovarian cancer cells: characterization of strutural elements required for growth factor function." Febs Letters, vol. 438, No. 1-2, Oct. 30, 1998, pp. 101-105, XP002143814 Amersterdam, die Niederland Abstract figure 3.
H. Allgayer et al.: "Immunocytochemical phenotyping of disseminated tumor cells in bone marrow by uPA and receptor and CK18: investigation of sensitivity and specificity of an immunogold/alkaline phosphatase double staining protocol" Journal of Histochemistry and Cytochemistry, vol. 45, no. 2, Feb. 1997, Baltimore, MD, USA cited in the application abstract.
M. Heiss et al.: "indivdual development and uPA-receptor expression of disseminated tumour cells in bone marrow: a reference to early systemic disease in solid cancer" Nature Medicine, vol. 1, No. 10, Oct. 1995, pp. 1035-1039, XP02117248 New York, NY, USA cited in the application p. 1039, column 1, line 18, paragraph 2—line 39.
I. Funke et al.: "comparative analyses of bone marrow micrometastases in breast and gastric cancer" International Journal of Cancer, vol. 65, No. 6, Mar. 15, 1996, pp. 755-761, XP002117249 New York, NY, USA cited in the application abstract.
R. Ciccocioppo et al.: "Detection of the receptor for the human urokinase-type flouresceinated uPA" Journal of Histochemistry and Cytochemistry, vol. 45, No. 9, Sep. 1997, Baltimore, MD, USA cited in the application figures 1, 2.

* cited by examiner

Primary Examiner—Sheela J. Huff
(74) Attorney, Agent, or Firm—Rothwell, Figg, Ernst & Manbeck, P.C.

(57) ABSTRACT

The invention concerns a method and a reagent kit for detecting cells in a biological sample using a double-fluorescence technique and the diagnostic and therapeutic application of amino acid sequence-specific antibodies against the urokinase receptor having a high affinity for tumour cell-expressed receptors.

Figure 1:
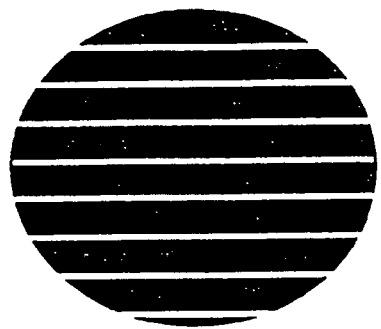
Figure 1:
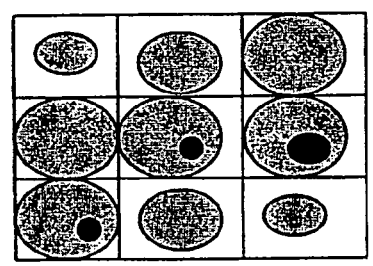
Figure 1:
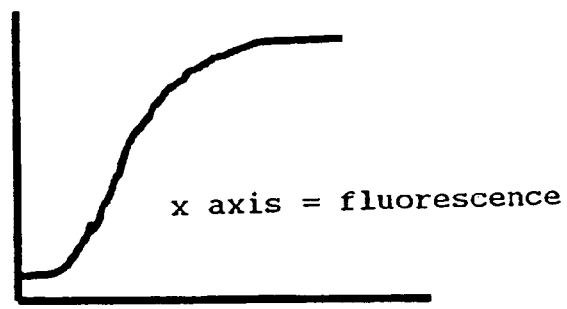

6 Claims, 14 Drawing Sheets a b c a b a b a b c a b c

A

B

SEQUENCE LISTING

```
<160> NUMBER OF SEQ ID NOS: 6

<210> SEQ ID NO 1
<211> LENGTH: 354
<212> TYPE: DNA
<213> ORGANISM: Artificial Sequence
<220> FEATURE:
<223> OTHER INFORMATION: phage sequence
```

```
<220> FEATURE:
<221> NAME/KEY: CDS
<222> LOCATION: (1)..(354)

<400> SEQUENCE: 1 cag gtg caa ctg cag cag tca gga cct gag ttg gtg aag cct ggg gct      48
Gln Val Gln Leu Gln Gln Ser Gly Pro Glu Leu Val Lys Pro Gly Ala
 1               5                  10                  15 tta gtg aag ata tcc tgc aag gct tct ggt tac agt ttc aca agc tac      96
Leu Val Lys Ile Ser Cys Lys Ala Ser Gly Tyr Ser Phe Thr Ser Tyr
             20                  25                  30 gat ata aat tgg gtg aag cgg agg cct gga cag gga ctt gag tgg att     144
Asp Ile Asn Trp Val Lys Arg Arg Pro Gly Gln Gly Leu Glu Trp Ile
         35                  40                  45 gga tgg att ttt cct gga gat ggt agt acc aat tac aat gag aaa ttc     192
Gly Trp Ile Phe Pro Gly Asp Gly Ser Thr Asn Tyr Asn Glu Lys Phe
     50                  55                  60 aag gac aag gcc aca ctg act gct gac aaa tcc tcc agc aca gcc tac     240
Lys Asp Lys Ala Thr Leu Thr Ala Asp Lys Ser Ser Ser Thr Ala Tyr
 65                  70                  75                  80 atg cag ctc aac agc ctg act tct gag aac tct gca gtc tat ttc tgt     288
Met Gln Leu Asn Ser Leu Thr Ser Glu Asn Ser Ala Val Tyr Phe Cys
                 85                  90                  95 gca aga gat gga agt atg ggg ggg ttt gac tac tgg ggc caa ggg acc     336
Ala Arg Asp Gly Ser Met Gly Gly Phe Asp Tyr Trp Gly Gln Gly Thr
            100                 105                 110 acg gtc acc gtc tcc tca                                             354
Thr Val Thr Val Ser Ser
            115

<210> SEQ ID NO 2
<211> LENGTH: 118
<212> TYPE: PRT
<213> ORGANISM: Artificial Sequence
<220> FEATURE:
<223> OTHER INFORMATION: phage sequence

<400> SEQUENCE: 2

Gln Val Gln Leu Gln Gln Ser Gly Pro Glu Leu Val Lys Pro Gly Ala
 1               5                  10                  15

Leu Val Lys Ile Ser Cys Lys Ala Ser Gly Tyr Ser Phe Thr Ser Tyr
             20                  25                  30

Asp Ile Asn Trp Val Lys Arg Arg Pro Gly Gln Gly Leu Glu Trp Ile
         35                  40                  45

Gly Trp Ile Phe Pro Gly Asp Gly Ser Thr Asn Tyr Asn Glu Lys Phe
     50                  55                  60

Lys Asp Lys Ala Thr Leu Thr Ala Asp Lys Ser Ser Ser Thr Ala Tyr
 65                  70                  75                  80

Met Gln Leu Asn Ser Leu Thr Ser Glu Asn Ser Ala Val Tyr Phe Cys
                 85                  90                  95

Ala Arg Asp Gly Ser Met Gly Gly Phe Asp Tyr Trp Gly Gln Gly Thr
            100                 105                 110

Thr Val Thr Val Ser Ser
            115

<210> SEQ ID NO 3
<211> LENGTH: 324
<212> TYPE: DNA
<213> ORGANISM: Artificial Sequence
<220> FEATURE:
<223> OTHER INFORMATION: phage sequence
```

<220> FEATURE:
<221> NAME/KEY: CDS
<222> LOCATION: (1)..(324)

<400> SEQUENCE: 3

```
gat gtt ttg atg acc caa act cca aaa ttc atg tcc aca tca gta gga       48
Asp Val Leu Met Thr Gln Thr Pro Lys Phe Met Ser Thr Ser Val Gly
1               5                  10                  15 gac agg gtc agc atc acc tgc aag gcc agt cag aat gtt cgt act act       96
Asp Arg Val Ser Ile Thr Cys Lys Ala Ser Gln Asn Val Arg Thr Thr
             20                  25                  30 gta gcc tgg tat caa gag aaa cca ggg cag tct cct aaa gca ctg att      144
Val Ala Trp Tyr Gln Glu Lys Pro Gly Gln Ser Pro Lys Ala Leu Ile
         35                  40                  45 tac ttg gca tcc aac cgg cac act gga gtc cct gat cgc ttc aca ggc      192
Tyr Leu Ala Ser Asn Arg His Thr Gly Val Pro Asp Arg Phe Thr Gly
     50                  55                  60 agt gga tct gga aca gat ttc act ctc acc att agc aat gtg caa tct      240
Ser Gly Ser Gly Thr Asp Phe Thr Leu Thr Ile Ser Asn Val Gln Ser
65                  70                  75                  80 gaa gac ctg gca gat tat ttc tgt ctg caa cat tgg aat tat ccg tac      288
Glu Asp Leu Ala Asp Tyr Phe Cys Leu Gln His Trp Asn Tyr Pro Tyr
                 85                  90                  95 acg ttc gga ggg ggc acc aag ctg gaa atc aaa cgg                      324
Thr Phe Gly Gly Gly Thr Lys Leu Glu Ile Lys Arg
            100                 105
```

<210> SEQ ID NO 4
<211> LENGTH: 108
<212> TYPE: PRT
<213> ORGANISM: Artificial Sequence
<220> FEATURE:
<223> OTHER INFORMATION: phage sequence

<400> SEQUENCE: 4

```
Asp Val Leu Met Thr Gln Thr Pro Lys Phe Met Ser Thr Ser Val Gly
1               5                  10                  15

Asp Arg Val Ser Ile Thr Cys Lys Ala Ser Gln Asn Val Arg Thr Thr
             20                  25                  30

Val Ala Trp Tyr Gln Glu Lys Pro Gly Gln Ser Pro Lys Ala Leu Ile
         35                  40                  45

Tyr Leu Ala Ser Asn Arg His Thr Gly Val Pro Asp Arg Phe Thr Gly
     50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Tyr
                 85                  90                  95

Thr Phe Gly Gly Gly Thr Lys Leu Glu Ile Lys Arg
            100                 105
```

<210> SEQ ID NO 5
<211> LENGTH: 9
<212> TYPE: PRT
<213> ORGANISM: Artificial Sequence
<220> FEATURE:
<223> OTHER INFORMATION: CDR3-VH sequence

<400> SEQUENCE: 5

```
Asp Gly Ser Met Gly Gly Phe Asp Tyr
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: CDR3-LH sequence

<400> SEQUENCE: 6

Leu Gln His Trp Asn Tyr Pro Tyr Thr
1               5
```

DIAGNOSTIC AND THERAPEUTIC USE OF ANTIBODIES AGAINST THE UROKINASE RECEPTOR

CROSS-REFERENCE TO RELATED APPLICATION

This application is a National Stage entry of International Application No. PCT/EP00/03347, filed Apr. 13, 2000, the entire specification claims and drawings of which are incorporated herewith by reference.

The invention concerns a method and a reagent kit for detecting cells in a biological sample using a double-fluorescence technique.

The reliable detection of disseminated tumour cells which have escaped from a solid tissue structure (micrometastases) is of major importance for tumour diagnostics and treatment. Hence various methods have been developed over the past years to detect such individual disseminated tumour cells in body fluids or tissue samples. They can for example be detected by selectively labelling the rare cells by means of immunocytochemical methods in which case enzymatic labelling groups such as alkaline phosphatase are often used. Double labelling techniques are also known.

A publication by Schlimok et al. (Proc. Natl. Acad. Sci. USA 84 (1987) 8672–8676) describes the detection of micrometastatic tumour cells in bone marrow by means of a double-labelling technique in which a cytokeratin 18 antibody which is specific for cells of epidermal origin and a leucocyte antibody are used. In this method alkaline phosphatase and a radioactive labelling group ($^{125}$I) are used. Since there are drawbacks associated with the use of radioactive labelling groups, this method is not suitable for clinical practice.

Funke et al. (Int. J. Cancer 65 (1996), 755–761) describe the detection of micrometastases in bone marrow by means of a double-labelling technique using a cytokeratin 18 antibody and an E-cadherin antibody. Both antibodies are detected by means of alkaline phosphatase as an enzymatic labelling group and two differently coloured chromogenic substrates. However, the sequential detection of both antibodies by different chromogenic substrates is complicated and hence less suitable for clinical practice.

Heiss and co-workers (Heiss et al., Nature Med. 1 (1995), 1035–1039 and Allgayer et al., J. Histochem. Cytochem. 45 (1997), 203–212) detect disseminated tumour cells in bone marrow by means of a double-labelling method based on the simultaneous detection of cytokeratin 18 and the uPA receptor (uPAR). For this cells bound and fixed on a microscope slide are incubated with a biotinylated cytokeratin-specific antibody and subsequently with a conjugate of alkaline phosphatase and streptavidin. An enzymatic staining reaction is carried out using the immobilized alkaline phosphatase and a chromogenic substrate to form a dark-red stain. In addition a monoclonal antibody against uPAR is used which is labelled with a gold-conjugated secondary antibody and subsequently subjected to a silver enhancement reaction which results in a black stain. The microscope slides are then manually and visually screened for the stains (dark-red/black) under a microscope but a double stain is extremely difficult to detect.

The object of the present invention was to carry out a method for the detection of cells in particular of rarely occurring cells such as tumour cells in a biological sample e.g. bone marrow which at least partially eliminates the disadvantages of the prior art. In particular the method should at the same time be highly sensitive and enable a troublefree evaluation.

This object is achieved by a method for detecting cells in a biological sample which comprises the following steps:

(a) preparing a sample to be tested,
(b) contacting the sample with at least two different binding molecules which recognize the cells to be detected, the binding molecules being each labelled with different fluorescent dyes and
(c) determining the fluorescent labels in the sample fixed on a solid phase.

The method according to the invention is suitable for detecting rarely occurring cells in a fixed biological sample. In this connection "rarely occurring" in the sense of the present invention means that the expected frequency of the cells to be detected is in the range of $1:10^4$ to $1:10^7$ of the total number of cells present in the sample to be detected. Examples of such rarely occurring cells are tumour cells in a blood or bone marrow sample. Other types of rarely occurring cells can of course also be detected if the cell-specific determinants and specific binding molecules are selected accordingly.

The double-fluorescent staining technique of the method according to the invention allows a rapid and accurate identification of the cells to be detected. In addition the use of different fluorescent labels that can be preferably detected concurrently enables antigens to be analysed that are co-located in as well as on the cell (such as e.g. cytokeratin 8/18, p53, PAI-2 and in particular the urokinase receptor uPAR). This has previously been very difficult with the known methods especially in the case of tissue samples such as bone marrow aspirates. A further major advantage of the newly developed method is that it allows a quantitative determination of the number and intensity of fluorescent cells for example with a confocal laser scanning microscope.

Step (a) of the method according to the invention comprises the provision of a biological sample to be tested. For this a sample is taken from the patient e.g. from a body fluid such as blood or from a tissue such as bone marrow. The method according to the invention is particularly preferably used to detect disseminated tumour cells of epidermal origin in the bone marrow. The bone marrow can be taken from the iliac crest bone. Mononuclear cells including tumour cells are then preferably concentrated in the sample. This concentration can be carried out by known methods for example by density gradient centrifugation e.g. Ficoll in which a separation of erythrocytes and granulocytes occurs.

The sample to be tested preferably contains at least $10^6$ cells in order to enable a reliable detection of rare cells. The sample particularly preferably contains $10^6$ to $10^9$ and in particular $5 \times 10^6$ to $5 \times 10^7$ cells.

According to step (b) the sample is contacted with at least two different binding molecules that are directed against the cells to be detected. The binding molecules are preferably antibodies or antibody fragments and in particular monoclonal antibodies or antibody fragments. However, it is also possible to use ligands of receptors such as the uPA receptor that specifically occur in the cells to be detected. Examples of such ligands are linear or/and cyclic peptides or peptide mimetics which can carry a fluorescent label.

The sample is preferably contacted with the fluorescent-labelled binding molecules after the cells have been fixed on a solid phase. This fixation can be carried out by known methods e.g. using formaldehyde or glutardialdehyde. A microscope slide can for example be used as the solid phase.

If necessary the cells present in the sample to be tested can be permeabilized using a detergent such as a saponin. This enables the binding molecules to also bind to intracellular determinants.

For the detection of tumour cells the binding molecules are directed against determinants which only occur in tumour cells or are present at an increased concentration in tumour cells in the sample to be tested but do not occur in normal cells or only in a low concentration. A structure from the interior of the cells e.g. a cytokeratin is preferably selected as the first determinant. Cytokeratins are specific components of the cytoskeleton of epithelial cells and are not expressed in mononuclear blood or bone marrow cells which are of mesenchymal origin. Hence the presence of cytokeratins in cells which have been taken from blood and bone marrow indicates the presence of epithelial tumour cells. Examples of suitable anti-cytokeratin antibodies are the antibody A45B/B3 (Micromet GmbH, Munich, Germany) or the antibody CK2 (Boehringer Mannheim GmbH, Mannheim, Germany). Other detection antibodies directed against intracellular tumour-associated antigens are known and are commercially available from various companies.

A structure on the cell surface such as a membrane receptor is preferably selected as the second determinant. The urokinase receptor (uPAR) is a particularly preferred tumour-specific determinant. This receptor can for example be detected using anti-uPAR antibodies such as IID7 and IIIF10 (Luther et al., Am. J. Path. 150 (1997), 1231–1244). Those anti-uPAR antibodies are preferably selected which have an affinity for a tumour cell-specific uPAR which is at least comparable to that for a uPAR from normal cells. Examples of anti-uPAR antibodies which also bind to tumour cells with high affinity are antibodies which recognize the epitope 52–60 of uPAR such as the above-mentioned antibody IIIF10.

In contrast other anti-uPAR antibodies often only poorly recognize uPAR on tumour cells.

On the other hand uPAR can also be detected with fluorescent-labelled receptor ligands e.g. urokinase, urokinase fragments or urokinase peptides. Such detection methods are described for example by Chucholowski et al. (Fibrinolysis 6, Suppl. 4 (1992), 95–102), Ciccocioppo et al. (J. Histochem. Cytochem. 45 (1997), 1307–1313) and Luther et al. (Am. J. Pat. 150 (1997), 1231–1242).

At least two different fluorescent labelling groups are used in the method according to the invention. It is advantageous to use fluorescent labelling groups which have emission spectra (e.g. red/green) that can be distinguished from one another. Examples of suitable fluorescent dyes are fluorescein and derivatives thereof, phycoerythrin, rhodamine, TRITC-amines, Texas Red® amines, CY3 and CY5 as well as Alexa® 488 and Alexa® 568 (Molecular Probes). The fluorescent dyes can be directly e.g. covalently conjugated with the primary binding molecules that are specific for the cells to be detected. This is referred to as a direct label. On the other hand the fluorescent dyes can be conjugated to secondary binding molecules which are in turn directed against the primary binding molecules. This is referred to as an indirect label. Both labelling methods or combinations thereof can be used in the method according to the invention.

The various binding molecules can be sequentially or concurrently incubated with the cell. An incubation with several binding molecules in parallel (primary binding molecules and optionally secondary binding molecules in the case of an indirect label) leads to a considerable time saving.

The sample is evaluated by determining the fluorescence after exciting the fluorescent labelling groups. A confocal laser scanning microscope or a fluorescence microscope is particularly preferably used for this which enable an evaluation of the sample by concurrent or/and sequential determination of the various fluorescent labelling groups.

The double-fluorescence labelling technique according to the invention additionally enables a characterization of the cells identified as positive by reaction with the binding molecules. This characterization can comprise site-specific or/and quantitative evaluation of the label. Hence individual cells can be "scanned" by determining the label in several e.g. 10 to 50 planes of sections through the cell at distances of for example 0.1 to 1 µm. In addition the determinants in the cell that have reacted with the binding molecules can be determined quantitatively on the basis of a standard curve which has been constructed by measuring microparticles of a defined size and a defined amount of fluorescent dye.

The method according to the invention allows valuable diagnostic data to be obtained from tumour patients and hence enables a sensitive prognosis to be made for patients after operation of a primary tumour.

Finally the invention concerns a reagent kit for the detection of cells in a biological sample comprising
(a) a first binding molecule which recognizes the cells to be detected and a first fluorescent labelling group,
(b) a second binding molecule which recognizes the cells to be detected and a second fluorescent labelling group, the first and the second binding molecule and the first and the second fluorescent labelling group being different and
(c) means for fixing cells on a solid phase.

It was surprisingly found that uPAR antibodies which are directed against the epitope 52–60 of uPAR recognize a uPAR having a glycostructure that occurs in tumour cells i.e. bind to a uPAR expressed by tumour cells with an at least comparable affinity to a uPAR expressed by normal cells. In contrast other anti-uPAR antibodies e.g. HD13.1 (Todd et al., CD87 workshop panel report. In: Kishimoto T. et al., publ. Leucocyte Typing VI, New York & London, Garland Publishing, Inc. 1997; 1016–1020) only have a low affinity for uPAR from tumour cells.

Hence the invention concerns the use of an antibody or of an antigen-binding fragment thereof (preferably of a monoclonal antibody or of an antigen-binding fragment thereof) which is directed against the epitope 52 to 60 of uPAR to produce a diagnostic or therapeutic agent directed against uPAR on tumour cells. Such antibodies like the known monoclonal antibody IIIF10 (Luther et al. (1997), supra) or antibodies having an equivalent binding specificity such as chimerised or humanized antibodies or corresponding recombinant or proteolytic antibody fragments, e.g. single-chain antibody fragments, recognize a uPAR expressed by tumour cells with an adequate affinity for diagnostic and therapeutic purposes.

Furthermore it was surprisingly found that such antibodies or fragments thereof can be used as a diagnostic agent to predict the course of malignant diseases especially in the case of tumours e.g. breast carcinomas. In tumour samples from over 200 examined female breast carcinoma patients it was found that the binding of the antibody IIIF10 or of a corresponding antibody with an equivalent binding capability has a significant prognostic relevance for the course of the disease i.e. absence of recidivity or death. In this connection high antigen values indicate a shorter absence of recidivity or an earlier death. Such a prognostic significance was not found with antibodies which are directed against other regions of uPAR.

Due to their high affinity for tumour uPAR these antibodies or fragments thereof are also suitable as diagnostic agents for detecting tumour cells in a biological sample and in particular for detecting disseminated tumour cells in bone marrow. Such detection methods can for example be carried out as an ELISA or as previously elucidated in detail double-fluorescence detection methods.

Moreover antibodies which are directed against the epitope 52 to 60 of uPAR or fragments thereof are suitable for preparing a therapeutic agent with for example selective function blocking activity iN tumour cells. In addition the antibodies or fragments thereof can be used in the form of conjugates with a cytotoxic group to inhibit the growth of or kill tumour cells. Examples of suitable cytotoxic groups are radioactive groups, toxins and cell growth inhibitors. For therapeutic applications it is preferable to use chimeric antibodies with humanized constant domains the production of which is described for example in EP-B-0 120 694.

Yet a further subject matter of the invention are recombinant nucleic acids which code for a polypeptide with antibody properties and contain the CDR3-VH sequence or/and the CDR3-VL sequence of the antibody IIIF10. The CDR3 region of the VH cDNA is shown in SEQ ID NO.1/2 from nucleotide 295 to 321 (corresponding to amino acid 99 to 107). The CDR3 region of the VL cDNA is shown in SEQ ID NO.3/4 from nucleotide 265 to 291 (amino acid 89 to 97). In addition the nucleic acids preferably contain the sections of VH or/and VL cDNA coding for the CDR1 and/or CDR2 regions. The sequences for the CDR1-VH region are shown in SEQ ID NO.1/2 from nucleotide 91 to 105 (corresponding to amino acid 31 to 35, i.e. SYDIN). In SEQ ID NO.3/4 the CDR1 region of the VL cDNA extends from nucleotide 70 to 102 (corresponding to amino acid 24 to 34, i.e. KAS . . . TVA). The CDR2 region of the VH cDNA extends from nucleotide 148 to 198 (amino acid 50 to 66, i.e. WIF . . . FKD) in SEQ ID NO.1/2. The CDR2 region of the VL cDNA extends from nucleotide 148 to 168 (corresponding to amino acid 50 to 56, i.e. LASNRHT) in SEQ ID NO.3/4.

Thus the invention concerns in particular recombinant nucleic acids which code for a polypeptide having antibody properties comprising
(a) a CDR3-VH sequence coding for the amino acid sequence (I):

D G S M G G F D Y (SEQ ID NO: 5)

or/and
(b) a CDR3-VL sequence coding for the amino acid sequence (II):

L Q H W N Y P Y T (SEQ ID NO: 6)

Furthermore the invention concerns recombinant polypeptides having antibody properties comprising
(a) a CDR3-VH amino acid sequence (I):

D G S M G G F D Y (SEQ ID NO: 5)

or/and
(b) a CDR3-VL amino acid sequence (II):

L Q H W N Y P Y T (SEQ ID NO: 6)

The recombinant nucleic acids and polypeptides preferably contain the CDR3 regions of the VH as well as of the VL sequence. The recombinant polypeptides are particularly preferably single-chain antibodies e.g. scFv antibody fragments. In the recombinant polypeptides the framework domains which are not directly responsible for antigen binding are preferably replaced by corresponding human sequences such that humanized antibody fragments are formed. The recombinant polypeptides according to the invention can be coupled with effector groups i.e. cytotoxic groups for therapeutic applications or/and detection groups for a tumour imaging.

The invention is further elucidated by the following figures and examples.

FIG. 1: shows a diagrammatic view of the scanning of a cell in a laser microscope.
  a) A total of 30 serial sections with a spacing of 0.5 μm is prepared from a ca. 15 μm large tumour cell.
  b) The fluorescence is measured in each plane of the section and then all fluorescence values are added.
  c) The total fluorescence is calculated from a standard curve (latex microparticles containing a defined amount of fluorochrome).

Figure 2:
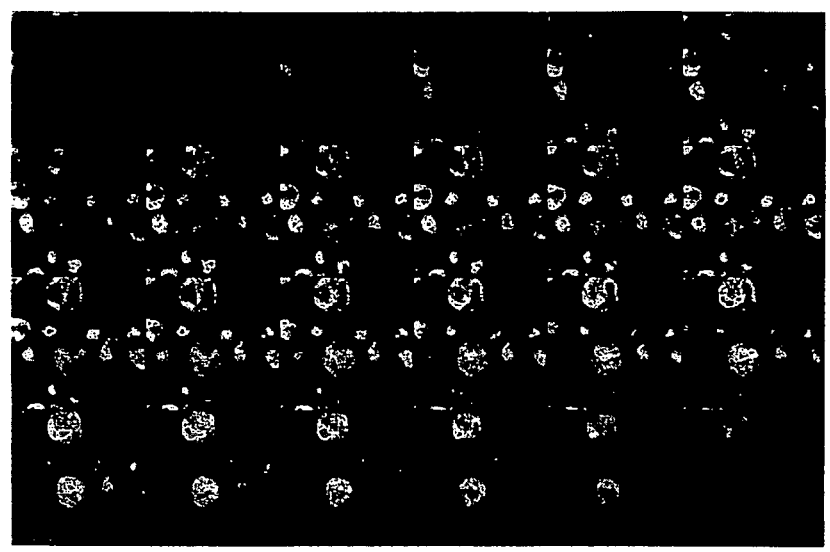
Figure 2:

FIG. 2: shows the result of the fluorescence staining of a tumour cell with the anti-cytokeratin antibody A45 B/B3 and Alexa 488 as a fluorescent dye.
  a) The sequence of images shows 24 photographs of a scan procedure in which a ca. 12 μm breast carcinoma cell (ZR75) was measured in section planes with a spacing of 0.5 μm in each case.
  b) shows an extended focus photograph in which the total intensity of the entire scan (a) has been projected onto a single image plane.

Figure 3:
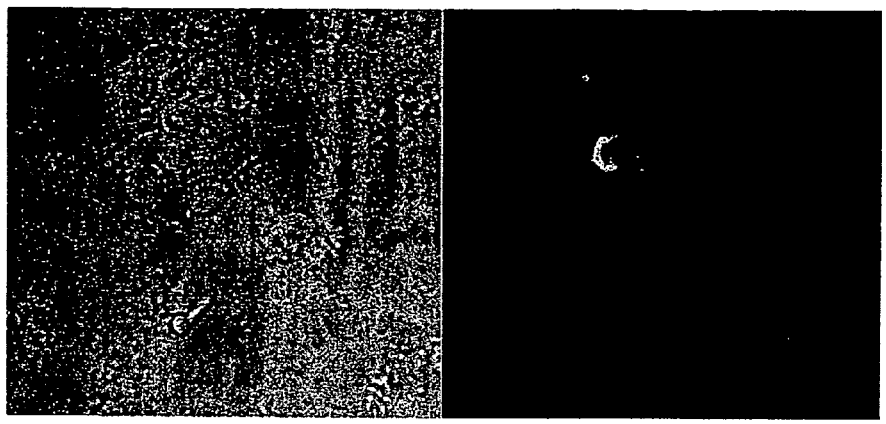
Figure 3:
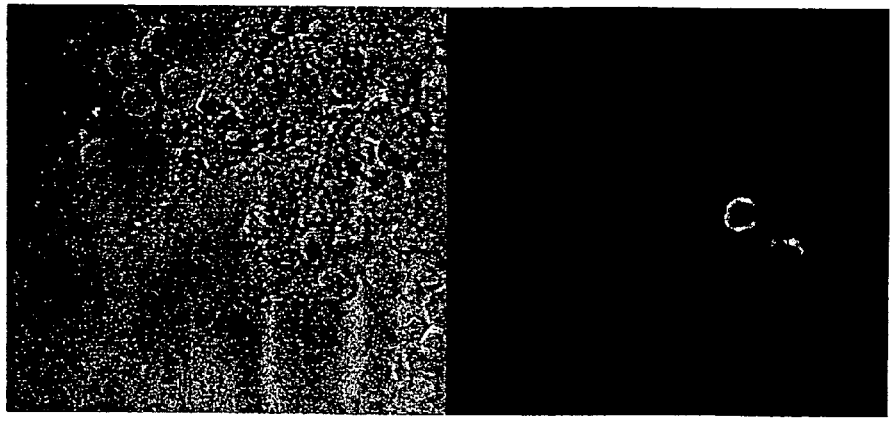

FIG. 3: shows the result of an indirect fluorescence staining with A45B/B3 as the primary antibody and a secondary antibody conjugated with Alexa 488 (enlargement ×63),
  a) transmission image
  b) a cytokeratin-positive cell in the bone marrow smear of a female patient with breast carcinoma.

Figure 4:
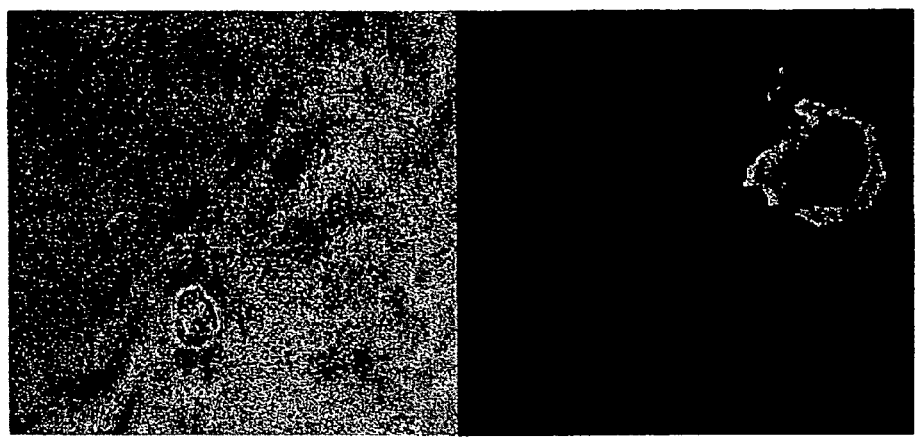
Figure 4:
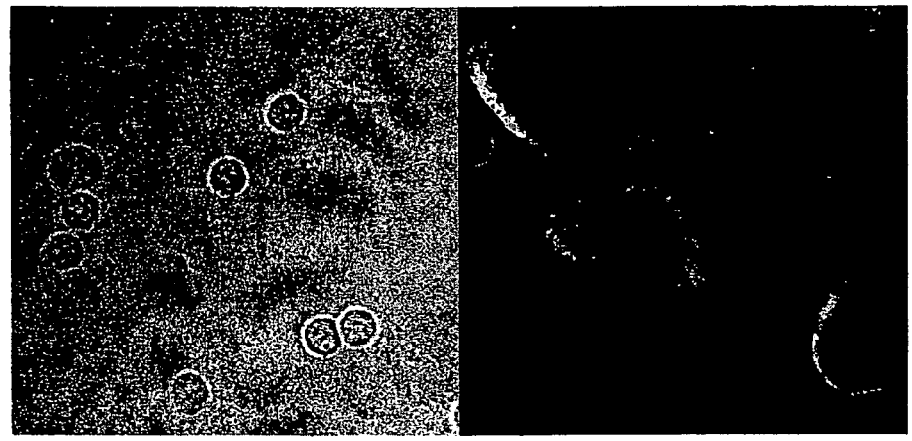

FIG. 4: shows the result of a direct fluorescence staining with a conjugate of the antibody A45B/B3 and the fluorescent dye Alexa 488 (enlargement ×63),
  a) transmission image
  b) cytokeratin detection in a mixed preparation of MCF7 tumour cells and peripheral blood lymphocytes (1:20).

Figure 5:
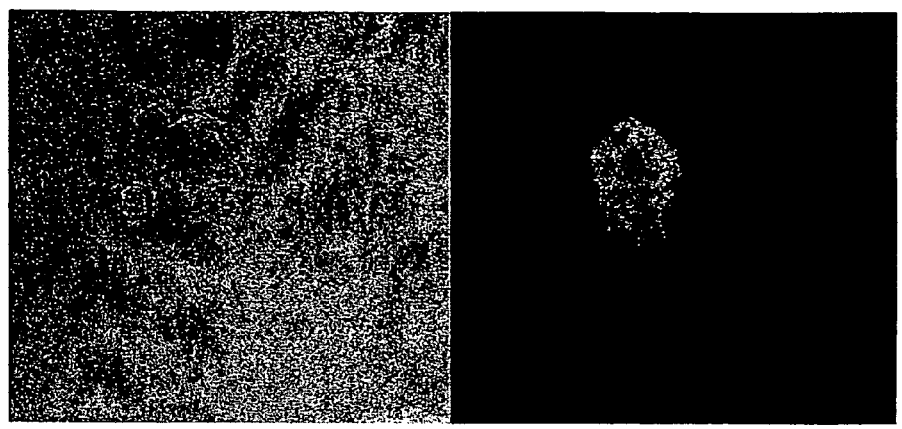
Figure 5:
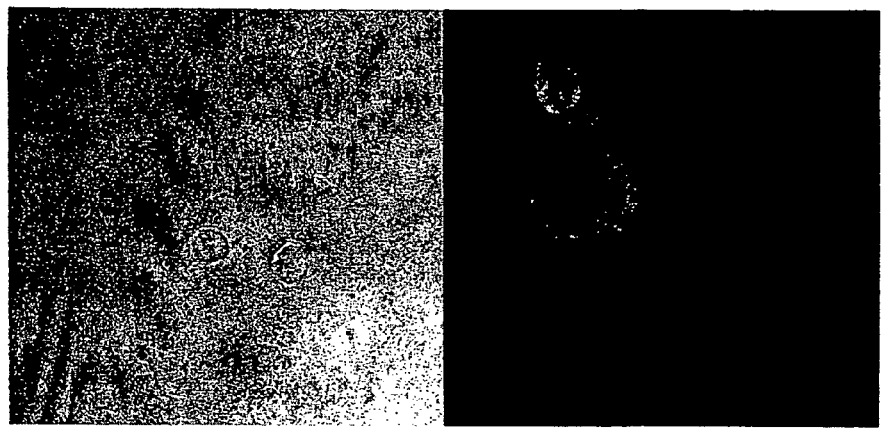

FIG. 5: shows the result of a direct fluorescence staining with a conjugate of the anti-uPAR antibody IIIF10 and the fluorescent dye Alexa 568 (enlargement ×63),
  a) transmission image
  b) uPAR receptor detection in a mixed preparation of MCF7 tumour cells and peripheral blood lymphocytes (1:20).

Figure 6:
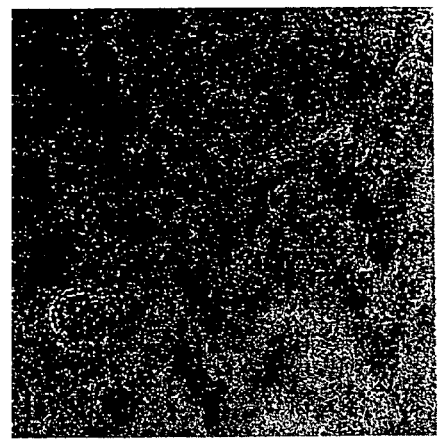
Figure 6:
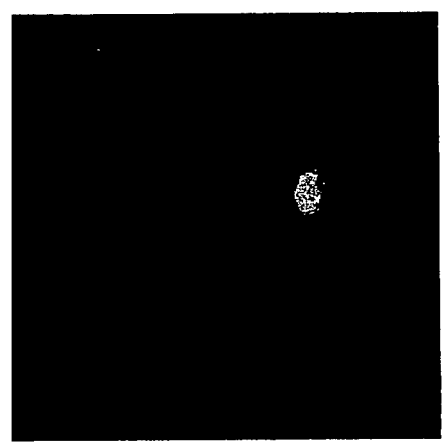
Figure 6:
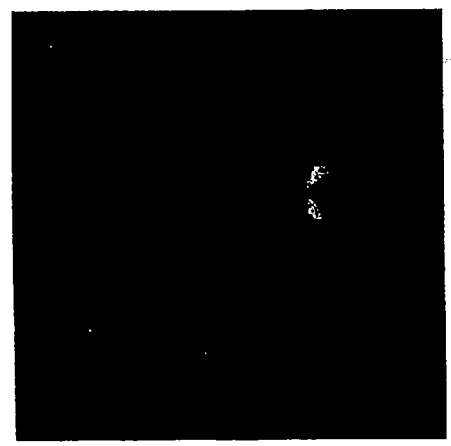
Figure 7:
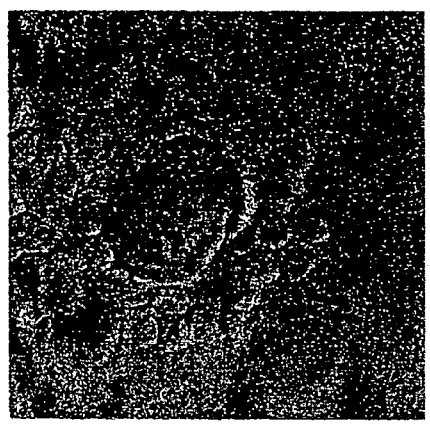
Figure 7:
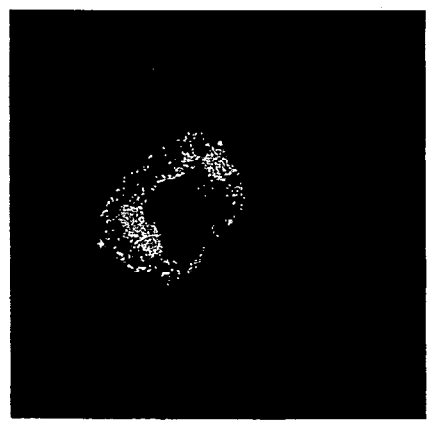
Figure 7:
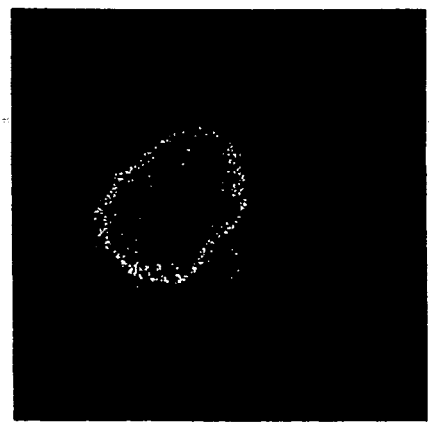

FIG. 6: shows the result of a direct double-fluorescence staining with the conjugates A45B/B3-Alexa 488 (anti-cytokeratin) and IIIF10-Alexa 568 (anti-uPAR),
  a) transmission image
  b) cytokeratin detection
  c) uPAR receptor detection FIG. 7: shows the result of the measurement of a tumour cell in the bone marrow (enlargement ×63),
  a) transmission image (Nomarski optics)
  b) reaction of the cell with a conjugate of Alexa 488 and an anti-cytokeratin antibody.
  c) reaction of the cell with a conjugate of Alexa 568 and a uPAR antibody. The cell nucleus is not stained. The reaction of the anti-uPAR antibody is mainly limited to the cell membrane. The uPAR-positive bone marrow cell which is negative for cytokeratin is shown on the bottom right. All other cells are uPAR-negative.

Figure 8:
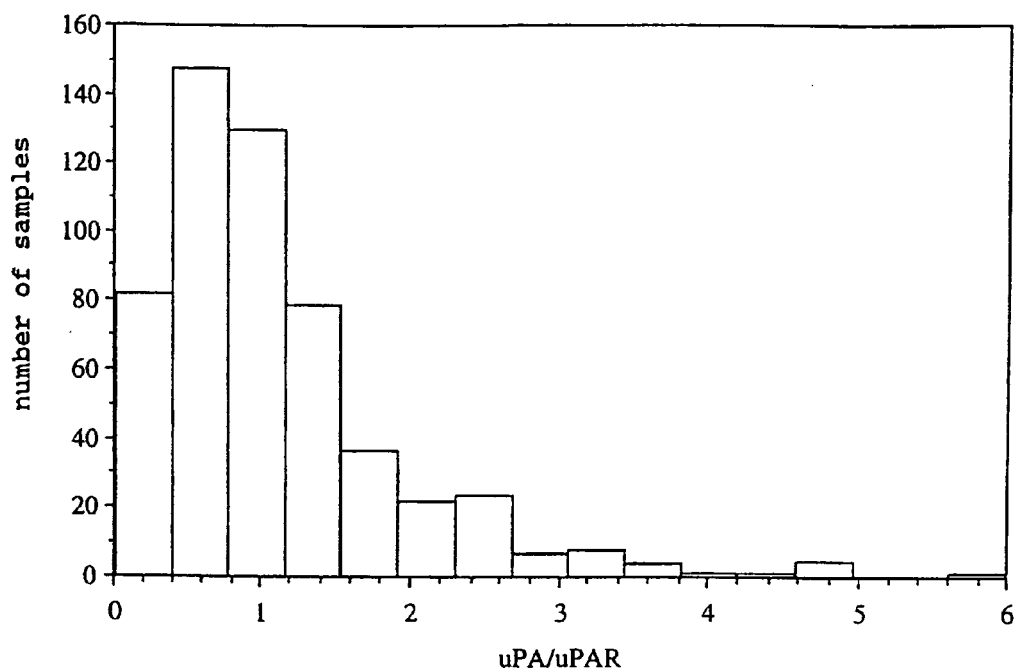
Figure 8:
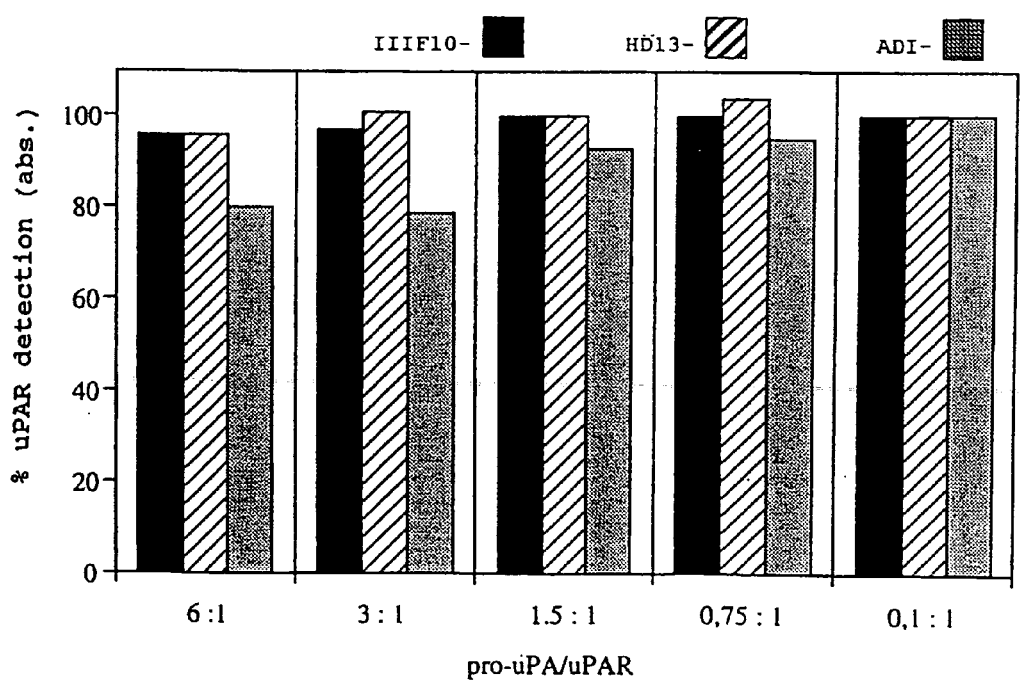

FIG. 8: shows the influence of uPA on the uPAR determination
  a) the UPA/uPAR ratio in tumour extracts from 599 breast carcinoma patients,
  b) the determination of uPAR in the presence of different amounts of uPA.

Figure 9:
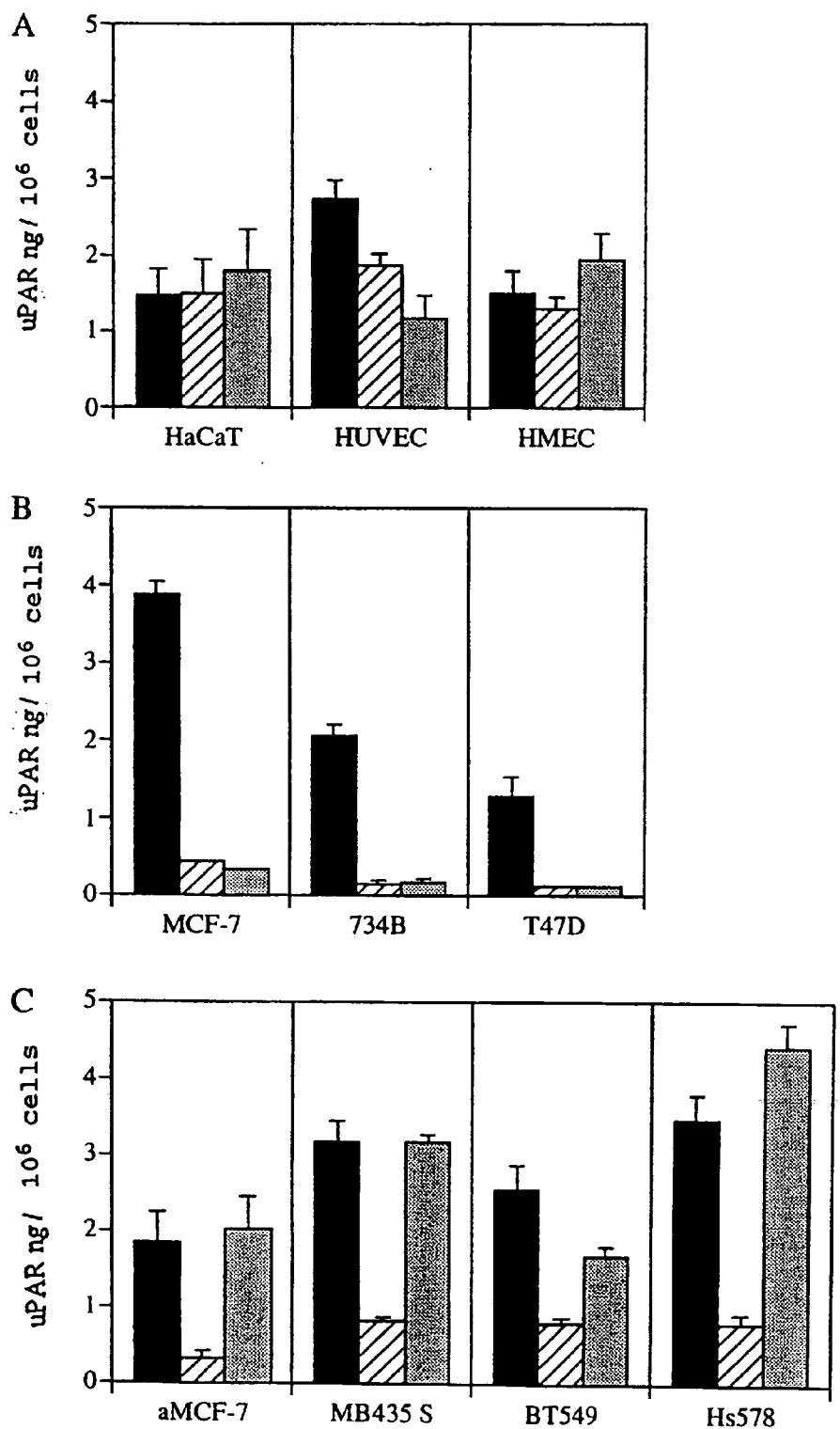

FIG. 9: shows the uPAR-antigen content in various cells determined by different test procedures:
IIIF10/HU277 black, HD13.1/HU277: dark grey, ADI light grey
a) normal cells
b) well-differentiated tumour cells
c) poorly-differentiated tumour cells FIG. 10: shows the prognostic relevance of the uPAR antigen content determined by various test procedures in 203 breast carcinoma patients
a) IIIF10/HU277
b) HD13.1/HU277
c) ADI FIG. 11: shows the dose-dependent inhibition of tumour growth of human breast cancer in naked mice by administering the antibody IIIF10.

Figure 12:
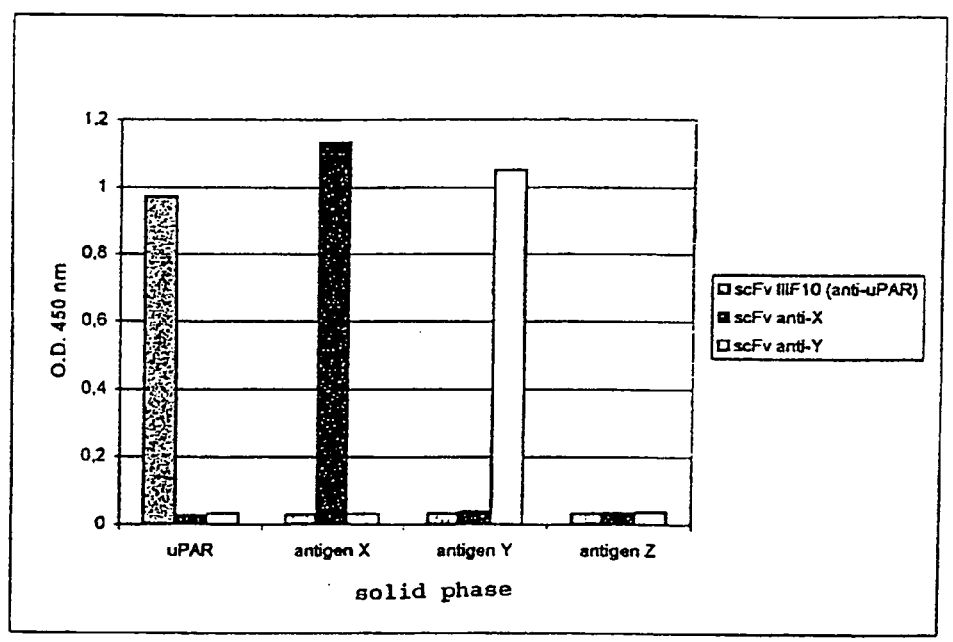

FIG. 12: shows the binding of scFv IIIF10 to immobilized antigens.

Figure 13:
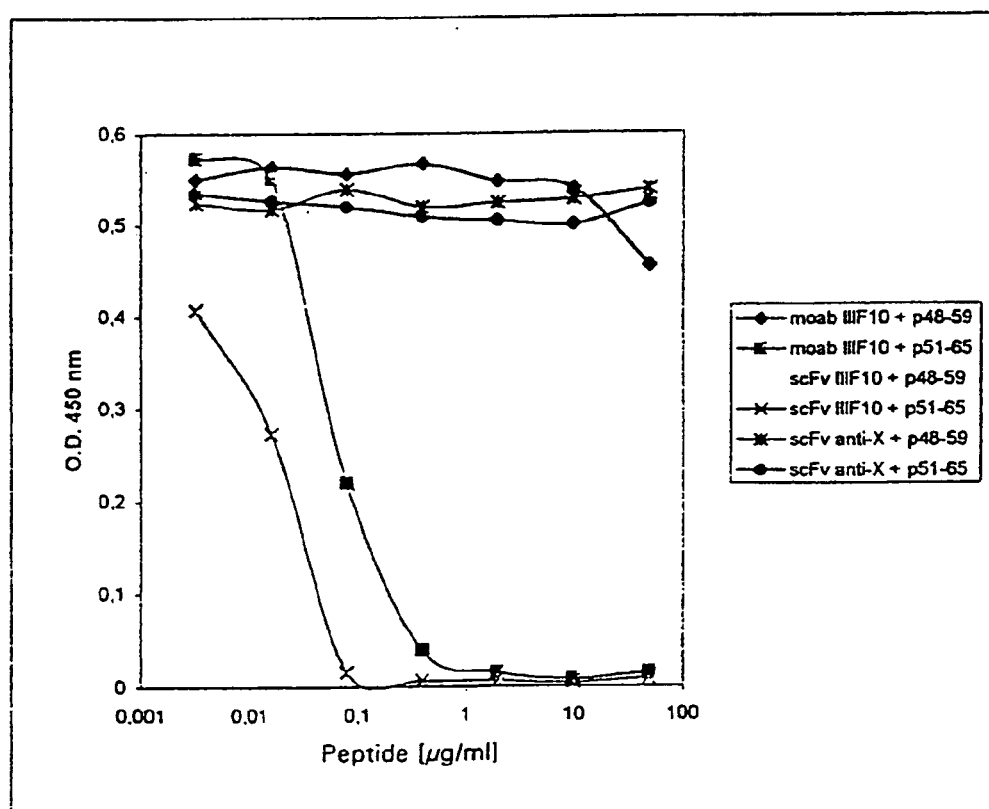

FIG. 13: shows the inhibition of the binding of IIIF10 (monoclonal antibody/moab and scFv) to uPAR by peptides.

SEQ ID NO 1/2: shows the nucleotide sequence of the cDNA coding for the VH chain of IIIF10 VH and the corresponding amino acid sequence.

SEQ ID NO 3/4: shows the nucleotide sequence of the cDNA coding for the VL chain of IIIF10 and the corresponding amino acid sequence.

EXAMPLES

1. Double-fluorescence Determination of Tumour Cells 1.1 Material

The monoclonal mouse antibody A45B/B3 (Kaspar et al., Eur. J. Cancer Clin. Oncol 23, (1987), 137–147) is directed against the cytokeratin filaments 8, 18 and 19 (CK 8, 18, 19). This antibody was directly conjugated with the fluorochrome ALEXA 488 from Molecular Probes. The uPA receptor is specifically detected by the monoclonal mouse antibody IIIF10 (Luther et al. (1997), supra) (epitope 52 to 60). The monoclonal antibodies HD13.1 and IID7 (Luther et al. (1997), supra) (epitope 125 to 132) as well as the polyclonal rabbit antibody #399R (Stahl et al., Cancer Res. 54 (1994), 3066–3071) and the chicken antibody HU277 (Magdolen et al., Electrophoresis 16 (1995), 813–816) are available as additional uPA receptor antibodies. All monoclonal antibodies against the uPA receptor were directly conjugated with the fluorescent dye ALEXA® 568.

TABLE 1

Directly conjugated antibodies that were used

| Monoclonal antibody | Antigen | directly conjugated with | excitation range in the CLSM* | Manufacturer |
|---|---|---|---|---|
| mAb II D 7 (mouse) | uPAR, domain 2 | ALEXA 568 (™Molecular Probes) | 568 nm | Pathology Dresden and Gynaecological Hospital Munich |
| mAb III F 10 (mouse) | uPAR, domain 1 | ALEXA 568 (™Molecular Probes) | 568 nm | Pathology Dresden and Gynaecological Hospital Munich |
| mAb HD 13.1 (mouse) | uPAR, domains 2 + 3 | ALEXA 568 (™Molecular Probes) | 568 nm | Immunology Heidelberg |
| mAB A45 B/B3 (mouse) | cytokeratin 8/9/18 | ALEXA 488 (™Molecular Probes) | 488 nm | Micromet Munich |

(*CLSM = confocal laser scanning microscope)

1.2 Bone Marrow Preparations

A Jamshidi puncture is carried out in the operating theatre. 4–6 ml bone marrow is taken from both iliac crests. The tumour cells in the mononuclear cell fraction are concentrated by means of a Ficoll gradient. 8 to 12 cytospins ($10^6$ cells by cytospin) are prepared per patient. After air-drying the preparations are fixed and permeabilized.

1.3 Fixation and Permeabilization
1. Fixation in 4% paraformaldehyde (PFA) for 30 min.
2. Wash three times in phosphate-buffered saline/1% bovine serum albumin (PBS/BSA).
3. Permeabilize in 0.025% saponin for 45 min.
4. Wash three times in PBS/1% BSA.

1.4 Double-labelling of the Cytokeratin and uPA Receptor 1.4.1. Indirect Method
1. Incubate overnight with the primary mouse antibody A45B/B3 (final concentration 0.004 mg/ml) in PBS/1% BSA.
2. Wash three times with PBS/1% BSA.
3. Incubate for two hours with the second primary rabbit antibody #399 R (final concentration 0.05 mg/ml) diluted in PBS/1% BSA.
4. Wash three times in PBS/1% BSA.
5. Secondary antibody goat anti-mouse-Alexa 488 (final concentration 0.02 mg/ml) diluted in PBS/1% BSA, incubation period 30 min.
6. Wash three times in PBS/1% BSA.
7. Secondary antibody goat anti-rabbit-Alexa 568 (final concentration 0.02 mg/ml) diluted in PBS/1% BSA, incubation period 30 min.
8. Wash three times in PBS/1% BSA.
9. Cover with 5 μl PBS/1% BSA and examine under a microscope.

1.4.2 Direct Method
1. Incubate for 1 hour with the antibody A45B/B3-Alexa 488 (final concentration 0.0014 mg/ml) diluted in PBS/1% BSA.
2. Wash three times in PBS/1% BSA.
3. Incubate for 1 hour with the antibody IIIF10-Alexa 568 (final concentration 0.003 mg/ml) diluted in PBS/1% BSA.
4. Wash three times in PBS/1% BSA.
5. Cover with 5 μl PBS/1% BSA and examine under a microscope.

1.5 Quantification

The antigens reacting with the fluorescent antibody are visualized in a confocal laser scanning microscope at an excitation range of 488 nm and 568 nm. The tumour cells are divided into 20 to 30 planes of section by scanning the cell in a laser microscope i.e. by layering in 0.5 μm steps. All fluorescences are detected and the sum of these measurements is calculated. The antigens in the tumour cell which have reacted with the antibody can be quantified on the basis of a standard curve which has been previously constructed by measuring latex beads containing a defined amount of fluorescent dye.

FIG. 1 shows a diagram of the principle of the scanning procedure used to localize and quantify the fluorescent label. FIGS. 2 to 7 show examples of results for the practical application of the method according to the invention.

2. Tumour Specificity of the Monoclonal Antibody IIIF10

Two different ELISA systems were developed for the detection of uPAR antigen:
1) Capture antibody: polyclonal chicken antibody HU277 (Magdolen et al. (1995), supra); detection antibody: monoclonal antibody IIIF10 (Luther et al. (1997), supra)
2) Capture antibody: polyclonal chicken antibody HU277; monoclonal antibody HD13.1 (Todd et al. (1997), supra).

These ELISA systems were compared with a commercially available ELISA (ADI) for uPAR (American Diagnostica Inc. Greenwich, Conn. USA).

The tested ELISA systems were matched using recombinant affinity-purified human uPAR (rec-uPAR) expressed in CHO cells. All three ELISA systems exhibited a comparable linearity and sensitivity towards rec-uPAR.

In further experiments it was demonstrated that the actual uPAR antigen content on cells can also be determined in the presence of an up to six-fold excess of uPAR. The recovery was>95% in the case of IIIF10/HU277 and the HD13.1/HU277 test and>80% in the case of the ADI test. The uPA/uPAR ratio in 599 analysed tumour extracts is typically <3 in 95% of the cases (tests with ADI-UPA and ADI-uPAR-ELISA). These results are shown in FIG. 8.

Subsequently the uPAR antigen contents were determined in lysates of various cell types. This showed that the determination of uPAR antigen in non-malignant cells (e.g. keratinocytes [HaCaT], endothelial cells from the umbilical cord [HUVEC], epithelial cells from the breast [HMEC] gave comparable results in all three ELISA systems. In contrast the situation was quite different in the case of tumour cell lines. In well-differentiated breast carcinoma cells only the IIIF10/HU277 ELISA detected significant amounts of tumour-associated uPAR whereas in poorly-differentiated breast carcinoma cell lines the IIIF10/HU277 and the ADI-ELISA gave comparable values. The HD13.1/HU277-ELISA detected too little uPAR in well-differentiated as well as in poorly-differentiated carcinoma cells. The data are shown in FIG. 9.

3. Prognostic Relevance of the Monoclonal Antibody IIIF10

Figure 10:
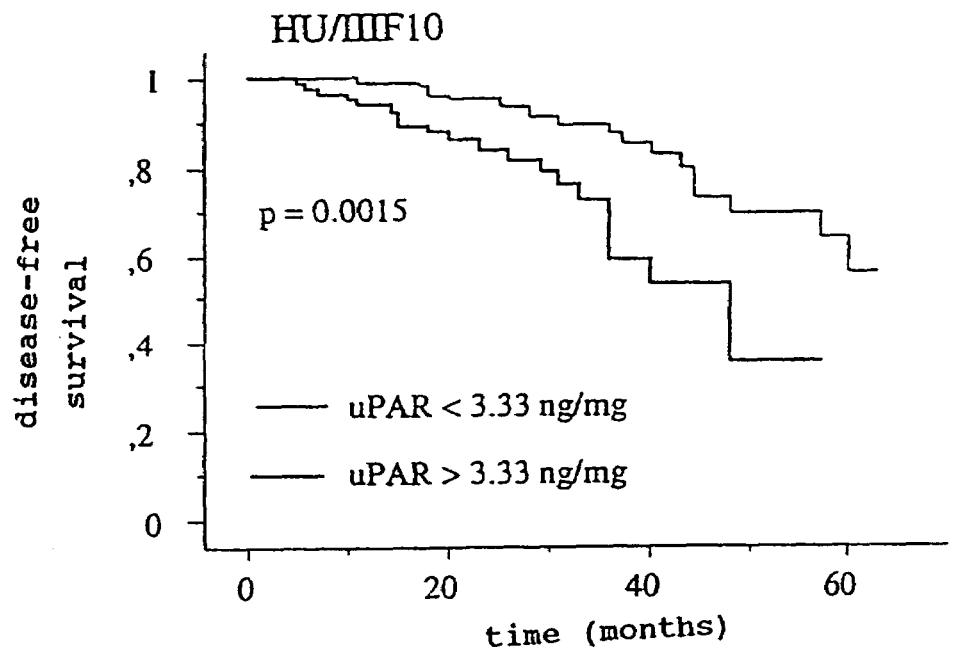
Figure 10:
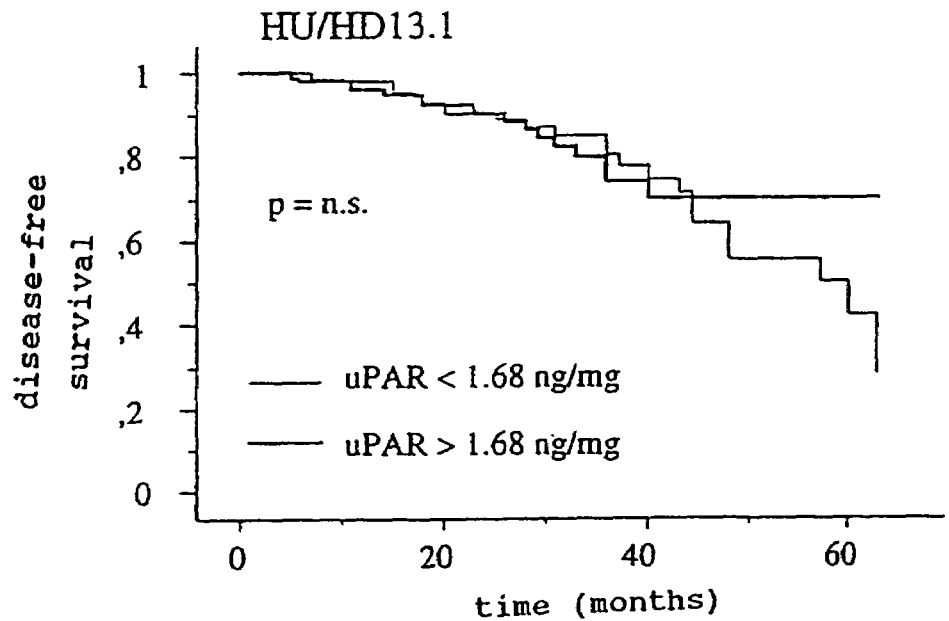
Figure 10:
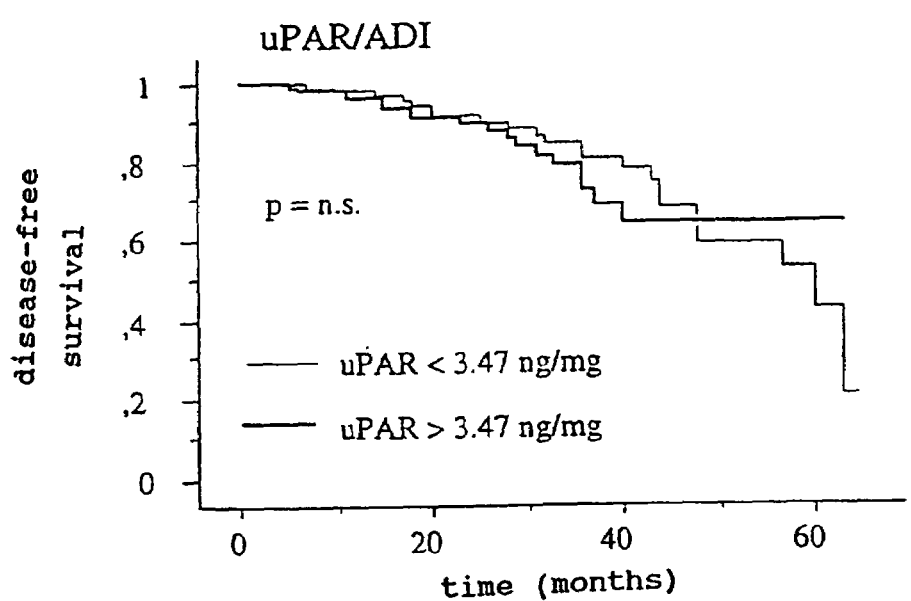

In a clinical study the uPAR antigen content was determined using all three ELISA systems described in example 2 in tumour samples from over 200 breast carcinoma patients. This showed that the antigen values measured with the IIIF10/HU277-ELISA have a significant prognostic relevance for the course of the disease i.e. for the absence of recidivity or death. Such a prognostic relevance was not found with the two other ELISA systems. The data are shown in FIG. 10.

4. In vivo Effect of the Monoclonal Antibody IIIF10

4 to 6 week old Balb/C/3 naked mice were injected on the right flank with $6 \times 10^6$ human breast cancer cells MDA-MB231 (Price et al., Cancer Res. 50 (1990), 717–721) in a total volume of 300 µl. Before injection the cancer cells were mixed in each case with 200 µg of the murine monoclonal antibody IIIF10 in PBS, pH 7.4. Subsequently the mice were treated intraperitoneally with the monoclonal antibody IIIF10 at a dose of 2 mg/kg body weight or 10 mg/kg body weight in an injection volume of 300 µl. The volume of the primary tumours in $cm^3$ occurring in the mice was determined after four weeks by measuring the two largest diameters of the tumours. PBS pH 7.4 was administered to the control mice, each group consisted of six mice.

Figure 11:
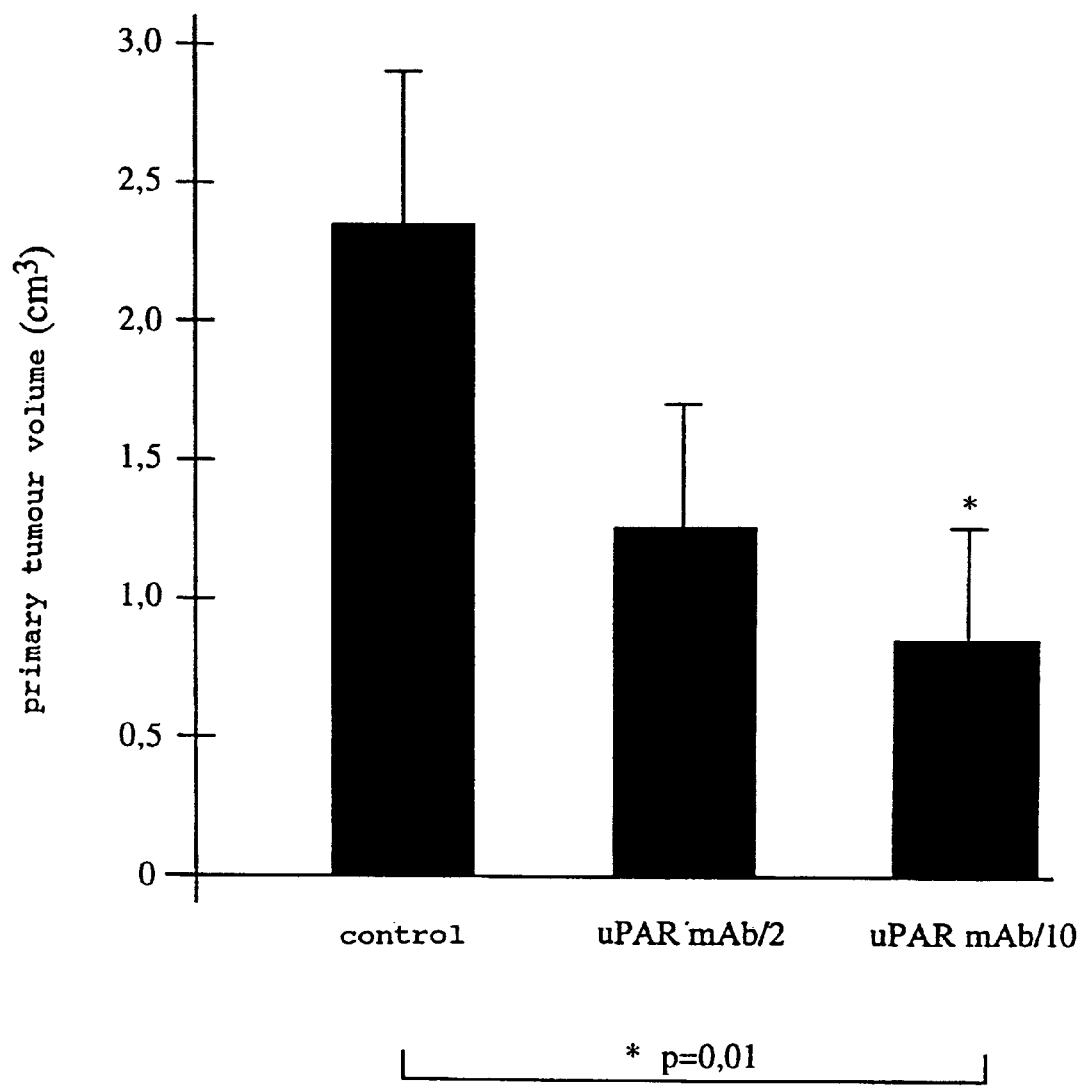

The results are shown in FIG. 11. It can be seen that the administration of the antibody greatly reduced the growth of primary tumours. The inhibition of growth was even more pronounced when 10 mg/kg body weight was administered than when a dose of 2 mg/kg body weight was administered.

5. Preparation of Recombinant Monoclonal Antibody IIIF10 mRNA from hybridoma cells producing IIIF10 was isolated and transcribed into cDNA. The cDNA fragments coding for the variable regions of the heavy (VH) and the light (VL) chain were amplified by RT-PCR using gene-specific primers. The VH and VL gene segments were cloned into a phagemid vector to enable expression of the variable regions as a single-chain antibody (scFv). The scFv molecules were presented by phage display on the surface of filamentous phages as a fusion protein containing the small phage coat protein pIII. Phages which exhibited a functional expression of scFv-FIII10 were selected by specific binding of uPAR. The selected phages were used to infect E. coli cells which enabled the production and secretion of soluble scFv molecules into the culture medium. FIG. 12 shows the binding of the scFv supernatant to uPAR immobilized on a solid phase. The binding capability of the antibodies scFv-anti-X and scFv-anti-Y was also tested for control purposes.

In order to further test the binding specificity, peptides were used which had been used to map the epitope of the antibody IIIF10 (Luther et al., J. Pathol 150 (1997), 1231–1244). As can be seen in FIG. 13 only one peptide the sequence of which contains the complete IIIF10 epitope on uPAR (51–65), can prevent the binding of the monoclonal antibody and of scFvIIIF10 to uPAR. Another peptide with an incomplete sequence epitope (48 to 59) is >100-fold less effective. None of the peptides can prevent the binding of a control antibody scFv-anti-X to its target protein X.

The nucleotide sequence of VH cDNA and the corresponding amino acid sequence are shown in SEQ ID NO. 1/2. The nucleotide sequence of the VL cDNA and the corresponding amino acid sequence are shown in SEQ ID No. 3/4.

The invention claimed is:

1. A method for determining the prognosis of the course of a malignant disease, comprising
   obtaining a sample from a subject suspected of containing tumor cells,
   contacting said sample with an antibody or an antigen-binding fragment thereof, which binds to the epitope 52–60 of the human urokinase receptor (uPAR), wherein a binding of the antibody or the antigen-binding fragment thereof with tumor cells in the sample is indicative of a tumor and gives a prognosis for the course of a malignant disease in said subject.

2. The method according to claim 1, wherein said tumor cells are disseminated tumor cells in bone marrow.

3. The method according to claim 1, wherein said sample is contacted with said antibody or an antigen-binding fragment in an ELISA.

4. The method according to claim 1, wherein said binding of the antibody or the antigen-binding fragment thereof with tumor cells is determined in a double-fluorescence detection method.

5. The method according to claim 1, wherein said antibody is the monoclonal antibody IIIF10, or antigen binding fragments thereof has the same binding specificity as monoclonal antibody IIIF10, or an antibody or antibody fragment having a binding specificity to the epitope 52–60 of uPAR.

6. The method according to claim 5, wherein said antibody comprises
   (a) a CDR3-VH amino acid sequence (I) D G S M G G F D Y (SEQ ID NO:5), and
   (b) a CDR3-VL amino acid sequence (II) L Q H W N Y P Y T (SEQ ID NO:6),
   (c) a CDR1-VH amino acid sequence S Y D I N (SEQ ID NO:7),
   (d) a CDR1-VL amino acid sequence K A S Q N V R T T V A (SEQ ID NO: 8),
   (e) a CDR2-VH amino acid sequence W I F P G D G S T N Y N E K F K D (SEQ ID NO: 9), and
   (f) a CDR2-VL amino acid sequence L A S N R H T (SEQ ID NO: 10).

* * * * *

UNITED STATES PATENT AND TRADEMARK OFFICE
CERTIFICATE OF CORRECTION

PATENT NO. : 7,157,238 B2 Page 1 of 1
APPLICATION NO. : 09/926323
DATED : January 2, 2007
INVENTOR(S) : Schmitt et al.

It is certified that error appears in the above-identified patent and that said Letters Patent is hereby corrected as shown below:

On the title page item [75] should read:

--Inventors: Manfred Schmitt; Frank Noack; Heinrich Graeff; Nadja Harbeck --.

Item [22] should read:

--(22) PCT Filed: April 13, 2000--

Signed and Sealed this

Twenty-second Day of May, 2007

JON W. DUDAS
*Director of the United States Patent and Trademark Office*